United States Patent
Breuil et al.

(10) Patent No.: US 10,633,303 B2
(45) Date of Patent: Apr. 28, 2020

(54) CATALYTIC COMPOSITION COMPRISING NICKEL AND A PHOSPHINE-TYPE LIGAND, AND USE THEREOF IN AN OLEFIN OLIGOMERISATION METHOD

(71) Applicant: IFP Energies Nouvelles, Rueil-Malmaison (FR)

(72) Inventors: Pierre-Alain Breuil, Lyons (FR); Olivia Chaumet-Martin, Brignais (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/747,793

(22) PCT Filed: Jul. 26, 2016

(86) PCT No.: PCT/EP2016/067756
§ 371 (c)(1),
(2) Date: Jan. 26, 2018

(87) PCT Pub. No.: WO2017/017087
PCT Pub. Date: Feb. 2, 2017

(65) Prior Publication Data
US 2018/0215681 A1 Aug. 2, 2018

(30) Foreign Application Priority Data
Jul. 29, 2015 (FR) ...................................... 1557247

(51) Int. Cl.
*C07C 2/36* (2006.01)
*B01J 31/24* (2006.01)
*B01J 31/14* (2006.01)

(52) U.S. Cl.
CPC ............... *C07C 2/36* (2013.01); *B01J 31/143* (2013.01); *B01J 31/24* (2013.01); *B01J 31/2404* (2013.01); *B01J 31/2409* (2013.01); *B01J 2231/20* (2013.01); *B01J 2531/847* (2013.01); *C07C 2531/14* (2013.01); *C07C 2531/20* (2013.01); *C07C 2531/24* (2013.01)

(58) Field of Classification Search
CPC ........................................................ C07C 2/36
USPC .................................. 585/510, 511, 512, 513
See application file for complete search history.

(56) References Cited

U.S. PATENT DOCUMENTS

| 3,513,218 | A | * | 5/1970 | Meyer Franz-Josef ...................... C07C 2/30 502/117 |
| 4,487,847 | A | | 12/1984 | Knudsen |
| 5,260,499 | A | | 11/1993 | Wu |
| 8,395,005 | B2 | * | 3/2013 | Coleman ................... C07C 2/36 585/324 |
| 2001/0051758 | A1 | * | 12/2001 | Fukuda ..................... B01J 31/04 585/510 |
| 2003/0125485 | A1 | * | 7/2003 | Brookhart ............. C07F 15/006 526/126 |
| 2009/0099059 | A1 | * | 4/2009 | Kuppert ................... C07C 2/465 512/8 |
| 2013/0018214 | A1 | * | 1/2013 | Zheng .................... B01J 31/143 585/513 |

FOREIGN PATENT DOCUMENTS

| EP | 1968918 A1 | 9/2008 |
| FR | 1588162 A | 4/1970 |
| FR | 2047213 A5 | 3/1971 |
| FR | 2895406 B1 | 8/2010 |
| GB | 1282305 A | 7/1972 |
| GB | 1411692 A | 10/1975 |

OTHER PUBLICATIONS

International Search Report PCT/EP2016/067756 dated Oct. 7, 2016.

* cited by examiner

*Primary Examiner* — Youngsul Jeong
(74) *Attorney, Agent, or Firm* — Millen, White, Zelano and Branigan, P.C.

(57) ABSTRACT

A process for the dimerization of ethylene to 1-butene, carried out with a catalytic composition comprising: at least one nickel precursor with an oxidation number of (+II), at least one phosphine ligand with formula $PR_1R_2R_3$ in which the groups $R_1$, $R_2$ and $R_3$ may be identical or different and which may or may not be bonded together, and at least one activating agent selected from the group formed by chlorinated and brominated hydrocarbylaluminium compounds, used alone or as a mixture, the composition having a molar ratio of the phosphine ligand to the nickel precursor in the range 5 to 30 and a molar ratio of the activating agent to the phosphine ligand greater than or equal to 1.

13 Claims, No Drawings

CATALYTIC COMPOSITION COMPRISING NICKEL AND A PHOSPHINE-TYPE LIGAND, AND USE THEREOF IN AN OLEFIN OLIGOMERISATION METHOD

The present invention relates to a process for the oligomerization of an olefin feed, comprising bringing said feed into contact with the nickel-based composition in accordance with the invention, and in particular to a process for the dimerization of ethylene to 1-butene using said nickel-based composition.

PRIOR ART

The transformation of ethylene using a homogeneous nickel catalyst has been studied since 1950. This research has led to the development and commercialization of various processes.

The development of catalytic systems capable of dimerizing ethylene to butenes involves selecting suitable metals and ligands. Of the existing systems, several nickel-based catalytic systems using phosphine-type ligands have been developed.

Thus, the U.S. Pat. No. 5,237,118 B describes a process for the oligomerization of ethylene using a catalytic composition comprising a nickel compound with an oxidation number of zero, and a phosphine ligand in proportions which vary with respect to the nickel compound. That patent also describes the use of an organic fluorinated acid for carrying out the oligomerization process.

The U.S. Pat. No. 4,242,531 B describes a process for the dimerization of olefins and employs a catalytic system based on chlorinated nickel compounds with an oxidation number of +2 and a halogenated alkylaluminium type activating agent. That patent is aimed at the production of 2-butenes.

The patent GB 1 282 305 A describes a process for the oligomerization of olefins in the presence of a catalytic composition based on a metal from group VIII, an electron donor such as phosphine and an aluminium compound. The molar ratio between the phosphine and the metal in the composition is in the range 0.5 to 18. However, the patent GB 1 282 305 A describes a process carried out at temperatures below 20° C. and preferably below 0° C.

The patent FR 1 547 921 describes a process for the oligomerization of olefins with a catalytic composition based on a nickel halide and phosphine which requires a prior reduction of the composition with a view to preparing the active catalyst. The yields of butenes are of the order of 63% C4, including 3% of 1-butenes.

The patent FR 1 588 162 describes a process for the dimerization of C2 to C4 olefins employing a catalytic system comprising a nickel compound and a phosphine, and in particular alkyl halides with butenes yields of the order of 80%. The molar ratio between the phosphine and the metal in the composition is in the range 1 to 5, however that patent is aimed at the production of 2-butenes.

The aim of the invention is to propose a novel process for the dimerization of ethylene to 1-butene which performs better in terms of yield and selectivity for the production of 1-butene.

The Applicant's research has led to the development of a novel process employing a catalytic composition comprising a nickel precursor with an oxidation number of (+II), at least one phosphine ligand, an optional Lewis base, and at least one activating agent, said process being characterized in that it is carried out at a temperature in the range from a value of more than 20° C. to +250° C. It has surprisingly been discovered that the process in accordance with the invention has a good yield/catalytic selectivity combination in the selective production of 1-butene.

DETAILED DESCRIPTION OF THE INVENTION

Composition in Accordance with the Invention

The catalytic composition used in the process of the invention comprises:
- at least one nickel precursor with an oxidation number of (+II),
- at least one phosphine ligand with formula $PR^1R^2R^3$, in which the groups $R^1$, $R^2$ and $R^3$, which may be identical or different, and which may or may not be bonded together, are selected from
  - aromatic groups, which may or may not be substituted and which may or may not contain heteroelements,
  - and/or hydrocarbyl groups, which may or may not be cyclic, which may or may not be substituted and which may or may not contain heteroelements,
- and at least one activating agent selected from the group formed by chlorinated and brominated hydrocarbylaluminium compounds, used alone or as a mixture, said composition having a molar ratio of the phosphine ligand to the nickel precursor in the range 5 to 30 and a molar ratio of the activating agent to the phosphine ligand which is greater than or equal to 1, preferably greater than or equal to 1.5, preferably greater than or equal to 2, the process being carried out at a temperature in the range from a value of more than 20° C. to +250° C.

Advantageously, in accordance with the invention, the catalytic composition comprises at least one phosphine ligand with formula $PR^1R^2R^3$ in which the groups $R^1$, $R^2$ and $R^3$ are identical.

The aromatic groups $R^1$, $R^2$ and $R^3$ of the phosphine ligand $PR^1R^2R^3$ are preferably selected from the group formed by the following groups: phenyl, o-tolyl, m-tolyl, p-tolyl, mesityl, 3,5-dimethylphenyl, 4-n-butylphenyl, 4-methoxyphenyl, 2-methoxyphenyl, 3-methoxyphenyl, 2 isopropoxyphenyl, 4-methoxy-3,5-dimethylphenyl, 3,5-di-tert-butyl-4-methoxyphenyl, 4-chlorophenyl, 3,5-di(trifluoromethyl)phenyl, benzyl, naphthyl, bisnaphthyl, pyridyl, bisphenyl, furanyl, and thiophenyl.

The hydrocarbyl groups $R^1$, $R^2$ and $R^3$ of the phosphine ligand $PR^1R^2R^3$ advantageously contain 1 to 20 carbon atoms, preferably 2 to 15 carbon atoms, more preferably between 3 and 10 carbon atoms. Preferably, the hydrocarbyl groups $R^1$, $R^2$ and $R^3$ of the phosphine ligand $PR^1R^2R^3$ are selected from the group formed by the following groups: methyl, ethyl, propyl, isopropyl, n-butyl, tert-butyl, cyclopentyl, cyclohexyl, benzyl, adamantyl.

The catalytic composition used in accordance with the invention may also comprise a Lewis base. In the context of the present invention, the term "Lewis base" is used to mean any chemical entity wherein one constituent has one or more free electron pairs or non-bonding electron pairs. The Lewis bases of the invention in particular correspond to any ligand comprising an oxygen or nitrogen atom with a free electron pair or non-bonding pair, or a π double bond which is capable of forming a $\eta^2$ type coordination with nickel.

Said Lewis base is preferably selected from diethylether, methyl tert-butylether, tetrahydrofuran, 1,4-dioxane, isoxazole, pyridine, pyrazine and pyrimidine.

In accordance with the invention, the activating agent used in the catalytic composition is selected from the group formed by chlorinated and brominated hydrocarbylaluminium compounds, used alone or as a mixture.

Advantageously, said activating agent is selected from the group formed by methylaluminium dichloride (MeAlCl$_2$), ethylaluminium dichloride (EtAlCl$_2$), ethylaluminium sesquichloride (Et$_3$Al$_2$Cl$_3$), diethylaluminium chloride (Et$_2$AlCl), diisobutylaluminium chloride (iBu$_2$AlCl), and isobutylaluminium dichloride (iBuAlCl$_2$), used alone or as a mixture.

Advantageously, the molar ratio of the phosphine ligand to the nickel precursor is in the range 5 to 25, preferably in the range 5 to 20, more preferably in the range 5 to 15. Preferably, this molar ratio is in the range 6 to 30, preferably in the range 6 to 25, more preferably in the range 6 to 20, still more preferably in the range 6 to 15, and even more preferably in the range 7 to 12.

Advantageously, the molar ratio of the activating agent to the phosphine ligand is preferably greater than or equal to 1.5, preferably greater than or equal to 2.

The molar ratio of the activating agent to the nickel precursor is preferably greater than or equal to 5, more preferably greater than or equal to 6, and preferably less than or equal to 30, preferably less than or equal to 25, more preferably less than or equal to 20.

The molar ratios cited in the present invention, in particular with respect to the nickel precursor, should be understood to be those expressed with respect to the number of moles of nickel provided in the catalytic composition.

The compositions used in the process in accordance with the invention may also optionally comprise a solvent. A solvent selected from organic solvents may be used, and in particular selected from ethers, alcohols, and saturated, unsaturated, aromatic or non-aromatic, cyclic or non-cyclic hydrocarbons. Preferably, the solvent is selected from hexane, cyclohexane, methylcyclohexane, heptane, butane or isobutane or any other hydrocarbon cut with boiling points of more than 70° C., preferably in the range 70° C. to 200° C. and preferably in the range 90° C. to 180° C., monoolefins or diolefins preferably containing 4 to 20 carbon atoms, cycloocta-1,5-diene, benzene, ortho-xylene, mesitylene, ethylbenzene, methanol, and ethanol, pure or as a mixture, and ionic liquids. In the case in which the solvent is an ionic liquid, it is advantageously selected from the ionic liquids described in the U.S. Pat. No. 6,951,831 B2 and FR 2 895 406 B1. Preferably, the solvent is selected from hexane, cyclohexane, methylcyclohexane, heptane, butane and isobutane or any other non-aromatic hydrocarbon cut with boiling points of more than 70° C., preferably in the range 70° C. to 200° C. and preferably in the range 90° C. to 180° C.

The nickel precursor of the composition used in the process in accordance with the invention has an oxidation number of +II. It is preferably selected from nickel(II) chloride, nickel(II)(dimethoxyethane) chloride, nickel(II) bromide, nickel(II)(dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates such as, for example, nickel 2-ethylhexanoate, nickel(II) phenates, nickel(II) naphthenates, nickel(II) acetate, nickel(II) trifluoroacetate, nickel(II) triflate, nickel (II) acetylacetonate, nickel(II) hexafluoroacetylacetonate, π-allyl nickel(II) chloride, π-allyl nickel(II) bromide, methallyl nickel(II) chloride dimer, η$^3$-allyl nickel(II) hexafluorophosphate, η$^3$-methallyl nickel(II) hexafluorophosphate and nickel(II) 1,5-cyclooctadienyl, in their hydrated or non-hydrated form, used alone or as a mixture.

Advantageously, the nickel precursor does not comprise halogenated compounds. Preferably, the nickel precursor is selected from nickel(II) sulphate, nickel(II) carbonate, nickel(II) dimethylglyoxime, nickel(II) hydroxide, nickel(II) hydroxyacetate, nickel(II) oxalate, nickel(II) carboxylates such as, for example, nickel 2-ethylhexanoate, nickel(II) phenates, nickel(II) naphthenates, nickel(II) acetate, nickel (II) trifluoroacetate, nickel(II) triflate, nickel(II) acetylacetonate, nickel(II) hexafluoroacetylacetonate, π-allyl nickel(II) chloride, π-allyl nickel(II) bromide, methallyl nickel(II) chloride dimer, η$^3$-allyl nickel(II) hexafluorophosphate, η$^3$-methallyl nickel(II) hexafluorophosphate and nickel(II) 1,5-cyclooctadienyl, in their hydrated or non-hydrated form, used alone or as a mixture.

The compositions described above are used in a process for the dimerization of ethylene to 1-butene.

The dimerization process in accordance with the invention may be operated in the presence of a solvent. In this case, the solvent may be selected from organic solvents, and preferably from saturated, unsaturated, cyclic or non-cyclic hydrocarbons. In particular, said solvent is selected from hexane, cyclohexane, methylcyclohexane, heptane, butane and isobutane, monoolefins or diolefins preferably containing 4 to 20 carbon atoms, pure or as a mixture, or any other non-aromatic hydrocarbon cut with boiling points of more than 70° C., preferably in the range 70° C. to 200° C. and more preferably in the range 90° C. to 180° C. In a preferred variation, at least a portion of the products obtained from the process are recycled to the dimerization process in accordance with the invention as a process solvent.

The solvent for the process may also be selected from ionic liquids. In the case in which said reaction solvent is an ionic liquid, it is advantageously selected from the ionic liquids described in the U.S. Pat. No. 6,951,831 B2 and FR 2 895 406 B1.

Advantageously, the various components of the catalytic composition, in particular the nickel precursor with an oxidation number of (+II), the phosphine ligand and the activating agent, are injected directly into the dimerization process in accordance with the invention, i.e. without an activation period. Preferably, each component is injected separately into the ethylene dimerization process in accordance with the invention. In a particular implementation, on the one hand a mixture of the nickel(II) precursor and the phosphine ligand and on the other hand the activating agent are separately injected into the ethylene dimerization process.

The olefins used as a feed in the process in accordance with the invention may be used alone or advantageously diluted with one or more alkane(s) or any other oil cut such as those found in "cuts" obtained from processes for the refining of oil or from petrochemistry, such as catalytic cracking or steam cracking.

Preferably, the olefin used as a feed in the oligomerization process is ethylene.

Said olefins used as a feed may derive from non-fossil sources such as biomass. As an example, the olefins used in the process in accordance with the invention may be produced from alcohols, and in particular by dehydration of alcohols.

The concentration of nickel in the catalytic solution, namely in the process in accordance with the invention, is advantageously in the range $1\times10^{-8}$ to 1 mol/L, preferably in the range $1\times10^{-6}$ to $1\times10^{-2}$ mol/L.

The process for the dimerization of ethylene to 1-butene is advantageously operated at a total pressure in the range from atmospheric pressure to 20 MPa, preferably in the range 0.1 to 8 MPa, more preferably in the range 3 to 8 MPa. The temperature of the process for the dimerization of ethylene to 1-butene is advantageously in the range −40° C. to +250° C., preferably between a value of more than 20° C. to 250° C., more preferably in the range 45° C. to 250° C., and still more preferably in the range 45° C. to 70° C.

It has surprisingly been discovered that when the process for the dimerization of ethylene to 1-butene is operated under the conditions of the invention and implemented with the composition in accordance with the invention, it has the advantage of producing 1-butene in a good yield/selectivity combination. Advantageously, the process in accordance with the invention can be used to obtain a butenes cut (C4) in a yield of at least 91% and a selectivity for 1-butene (1-C4) of at least 62%.

The heat generated by the reaction may be eliminated using any means known to the person skilled in the art.

The dimerization process may be carried out in a closed system, in a semi-open system or continuously, with one or more reaction stages. Vigorous stirring is advantageously carried out to ensure good contact between the reagent or reagents and the catalytic system.

The dimerization process may be carried out batchwise. In this case, a selected volume of the solution comprising the composition used in the process of the invention is introduced into a reactor which is preferably provided with the usual stirring, heating and cooling equipment.

The dimerization process may also be carried out continuously. In this case, the components of the composition in accordance with the invention are injected into a reactor in which the olefin, in particular ethylene, reacts, preferably under temperature control.

The catalytic composition used in the process of the invention is destroyed by any of the usual means known to the person skilled in the art, then the reaction products as well as the solvent are separated, for example by distillation. The olefin, in particular the ethylene which has not been transformed, may be recycled to the reactor.

The process in accordance with the invention may be carried out in a reactor having one or more reaction stages in series, the olefinic feed and/or the components of the catalytic composition being continuously introduced, either to the first stage or to the first and any other of the stages.

At the reactor outlet, the catalytic composition may be deactivated, for example by injecting an amine, which may or may not be diluted, and/or a basic aqueous solution and/or an aqueous acidic solution. The unconverted olefins and the alkanes which may be present in the feed are then separated from the oligomers by distillation.

The products of the present process may, for example, be of application as components of fuels for automobiles, as feeds in a hydroformylation process for the synthesis of aldehydes and alcohols, as components for the chemicals, pharmaceuticals or perfumery industries and/or as feeds in a metathesis process for the synthesis of propylene and/or as a feed for a process for the production of butadiene via oxidizing dehydrogenation or via a metallic catalysis step, for example.

The following examples illustrate the invention without limiting its scope.

EXAMPLES

Carrying Out the Catalytic Test:

The reactor was initially dried under vacuum and placed under an atmosphere of ethylene. 93 mL of n-heptane was introduced into the reactor under an atmosphere of ethylene. 6 mL of a solution containing the nickel precursor Ni(2-ethylhexanoate)$_2$ (denoted Ni(2-EH)$_2$, 5 or 10 μmol of the phosphine tri-n-butylphosphine or P(nBu)$_3$, tricyclohexylphosphine or PCy$_3$ or tri-isopropylphosphine or P(iPr)$_3$ (10, 20, 50 or 100 μmol) were then introduced into the reactor. Between 1 and 2 g of ethylene was then dissolved in the reactor, stirring was commenced and the temperature was programmed to 40° C. After degassing the reactor, the temperature was programmed to 45° C. (test temperature). 1 mL of a solution of ethylaluminium dichloride (75 or 150 μmol) was then introduced. The reactor was brought to the test pressure (2 MPa). The ethylene consumption was monitored up to the introduction of 50 g of ethylene. The ethylene supply was then cut off. The gas phase was quantified and qualified by gas phase chromatography (GC), and the liquid phase was weighed, neutralized and qualified by GC.

Catalytic Tests

Examples 1-2: Evaluation of the Ligand Tri-n-Butylphosphine P(nBu)$_3$

| Inflow | Catalytic precursor (Ni) | Ligand | Ligand/Ni molar ratio | Time (min) | Mass of C$_2$H$_4$ cons. (g) | % C4** | % C6 | % C8$^+$ | % 1-C4*** |
|---|---|---|---|---|---|---|---|---|---|
| 1* | Ni(2-EH)$_2$ | P(nBu)$_3$ | 2 | 10 | 40 | 89 | 10 | 1 | 47 |
| 2 | Ni(2-EH)$_2$ | P(nBu)$_3$ | 10 | 30 | 10 | 98 | 2 | 0 | 62 |

$n_{Ni}$ = 5 μmol, 15 eq. EtAlCl$_2$, 45° C., 2 MPa, 100 mL, n-heptane.
*Comparative example.
cons. = consumed.
**yield of C4 corresponding to the percentage by weight of the C4 cut formed in the products,
***percentage of 1-C4 in the C4 cut.

Examples 3-7: Evaluation of the Ligand Tricyclohexylphosphine (PCy$_3$)

| Inflow | Catalytic precursor | Ligand | Ligand/Ni molar ratio | Time (min) | Mass of C$_2$H$_4$ cons. (g) | % C4** | % C6 | % C8$^+$ | % 1-C4*** |
|---|---|---|---|---|---|---|---|---|---|
| 3* | Ni(2-EH)$_2$ | PCy$_3$ | 2 | 10 | 16 | 91 | 9 | 0 | 59 |
| 4*$^a$ | Ni(2-EH)$_2$ | PCy$_3$ | 10 | 60 | <1 | | not determined | | |

-continued

| Inflow | Catalytic precursor | Ligand | Ligand/Ni molar ratio | Time (min) | Mass of $C_2H_4$ cons. (g) | % C4** | % C6 | % $C8^+$ | % 1-C4*** |
|---|---|---|---|---|---|---|---|---|---|
| 5*$^b$ | Ni(2-EH)$_2$ | PCy$_3$ | 10 | 60 | <1 | | not determined | | |
| 6 | Ni(2-EH)$_2$ | PCy$_3$ | 10 | 40 | 20 | 96 | 4 | 0 | 97 |
| 7$^c$ | Ni(2-EH)$_2$ | PCy$_3$ | 10 | 10 | 41 | 93 | 7 | 0 | 81 |

$n_{Ni}$ = 5 µmol, 15 eq. EtAlCl$_2$, 45° C., 2 MPa, 100 mL, n-heptane.
*Comparative example.
$^a$Test carried out at 20° C. in chlorobenzene as reaction solvent.
$^b$ Test carried out at 20° C. in n-heptane as reaction solvent.
$^c n_{Ni}$ = 10 µmol.
cons. = consumed.
**yield of C4 corresponding to the percentage by weight of the C4 cut formed in the products,
***percentage of 1-C4 in the C4 cut.

Examples 8-9: Evaluation of the Ligand Tri-Isopropylphosphine P(iPr)$_3$

| Inflow | Catalytic precursor | Ligand | Ligand/Ni molar ratio | Time (min) | Mass of $C_2H_4$ cons. (g) | % C4** | % C6 | % $C8^+$ | % 1-C4*** |
|---|---|---|---|---|---|---|---|---|---|
| 8* | Ni(2-EH)$_2$ | P(iPr)$_3$ | 2 | 15 | 37 | 89 | 10 | 1 | 56 |
| 9 | Ni(2-EH)$_2$ | P(iPr)$_3$ | 10 | 16 | 36 | 94 | 6 | 0 | 89 |

$n_{Ni}$ = 10 µmol, 15 eq. EtAlCl$_2$, 45° C., 2 MPa, 100 mL, n-heptane.
*Comparative example.
cons. = consumed.
**yield of C4 corresponding to the percentage by weight of the C4 cut formed in the products,
***percentage of 1-C4 in the C4 cut.

It can be seen that the catalytic compositions in accordance with the invention (inflows 2, 6, 7 and 9) can be used to obtain a butenes cut (C4) in a yield of at least 93% and a selectivity for 1-butene (1-C4) of at least 62%, compared with the catalytic compositions which are not in accordance with the invention (inflows 1, 3, 8) which had a maximum yield of 91% of C4 and a selectivity for 1-butenes (1-C4) in the range 47% to 59%.

The invention claimed is:
1. A process for dimerization of ethylene to 1-butene comprising:
bringing ethylene into contact with a catalytic composition, wherein the catalytic composition comprises:
at least one nickel compound with an oxidation number of (II),
at least one phosphine ligand with formula PR$^1$R$^2$R$^3$, wherein the groups R$^1$, R$^2$ and R$^3$ are non-aromatic hydrocarbyl groups, the groups R$_1$, R$^2$ and R$^3$ are identical or different, the groups R$^1$, R$^2$ and R$^3$ may or may not be bonded together, the groups R$^1$, R$^2$ and R$^3$ may or may not be cyclic, the groups R$^1$, R$^2$ and R$^3$ may or may not be substituted, and the groups R$^1$, R$^2$ and R$^3$ may or may not contain heteroelements, and
at least one activating agent that is a chlorinated hydrocarbylaluminium compound that is methylaluminium dichloride (MeAlCl$_2$), ethylaluminium dichloride (EtAlCl$_2$), diethylaluminium chloride (Et$_2$AlCl), diisobutylaluminium chloride (iBu$_2$AlCl), isobutylaluminium dichloride (iBuAlCl$_2$), or a mixture thereof,
said catalytic composition having a molar ratio of the at least one phosphine ligand to the at least one nickel compound in a range of from 5 to 30 and a molar ratio of the at least one activating agent to the at least one phosphine ligand in a range of greater than or equal to 1; and
conducting the process for dimerization at a temperature in a range from greater than 20° C. to 250° C. thereby producing a product stream,
wherein, in the product stream, butenes are obtained in a selectivity for 1-butene of at least 62%.
2. The process according to claim 1, in which the groups R$^1$, R$^2$ and R$^3$ of said at least one phosphine ligand are identical.
3. The process according to claim 1, in which the groups R$^1$, R$^2$ and R$^3$ of the at least one phosphine ligand PR$^1$R$^2$R$^3$ are non-aromatic hydrocarbyl groups containing 1 to 20 carbon atoms.
4. The process according to claim 1, in which the groups R$^1$, R$^2$ and R$^3$ of the at least one phosphine ligand PR$^1$R$^2$R$^3$ are methyl, ethyl, propyl, isopropyl, n-butyl, tert-butyl, cyclopentyl, cyclohexyl, or adamantyl.
5. The process according to claim 1, in which the molar ratio of the at least one phosphine ligand to the at least one nickel compound is in a range of from 5 to 25.
6. The process according to claim 1, in which said catalytic composition also comprises a Lewis base.
7. The process according to claim 6, in which the Lewis base is diethylether, methyl tert-butylether, tetrahydrofuran, 1,4-dioxane, isoxazole, pyridine, pyrazine or pyrimidine.
8. The process according to claim 1, in which the at least one nickel compound is nickel(II) chloride, nickel(II)(dimethoxyethane) chloride, nickel(II) bromide, nickel(II)(dimethoxyethane) bromide, nickel(II) fluoride, nickel(II) iodide, nickel(II) sulphate, nickel(II) carbonate, nickel(II) dimethylglyoxime, nickel(II) hydroxide, nickel(II) hydroxyacetate, nickel(II) oxalate, nickel(II) carboxylates, π-allyl nickel(II) chloride, π-allyl nickel(II) bromide, methallyl nickel(II) chloride dimer, η$^3$-allyl nickel(II) hexafluorophosphate, η$^3$-methallyl nickel(II) hexafluorophosphate or nickel(II) 1,5-cyclooctadienyl, each optionally hydrated, or a mixture thereof.

9. The process according to claim 1, wherein the process for dimerization is carried out in a closed system, or in a semi-open system.

10. The process according to claim 1, wherein the at least one nickel compound is nickel (II) sulphate, nickel (II) carbonate, nickel(II) dimethylglyoxime, nickel(II) hydroxide, nickel (II) hydroxyacetate, nickel(II) oxalate, a nickel (II) carboxylate, a nickel (II) hexafluorophosphate or nickel (II) 1,5-cyclooctadienyl, each optionally hydrated, or a mixture thereof.

11. The process according to claim 1, wherein the at least one nickel compound is a nickel(II) carboxylate.

12. The process according to claim 1, wherein the at least one nickel compound, the at least one phosphine ligand and the at least one activating agent are injected separately into a reactor in which the ethylene is contacted with the catalytic composition.

13. The process according to claim 1, wherein the process for dimerization is carried out at a temperature of 45-70° C. and a pressure of 0.1 to 8 MPa.

* * * * *